United States Patent
Okumura

(10) Patent No.: US 8,148,357 B2
(45) Date of Patent: Apr. 3, 2012

(54) METHOD FOR THE PRODUCTION OF RESIN PARTICLES

(75) Inventor: Arimichi Okumura, Himeji (JP)

(73) Assignee: Daicel-Evonik Ltd., Tokyo (JP)

( * ) Notice: Subject to any disclaimer, the term of this patent is extended or adjusted under 35 U.S.C. 154(b) by 70 days.

(21) Appl. No.: 11/667,069

(22) PCT Filed: Sep. 13, 2005

(86) PCT No.: PCT/JP2005/016829
§ 371 (c)(1),
(2), (4) Date: May 4, 2007

(87) PCT Pub. No.: WO2006/061934
PCT Pub. Date: Jun. 15, 2006

(65) Prior Publication Data
US 2008/0199500 A1   Aug. 21, 2008

(30) Foreign Application Priority Data
Dec. 7, 2004   (JP) ................................ 2004-353956

(51) Int. Cl.
*A01N 43/00*   (2006.01)
(52) U.S. Cl. ....................................... 514/183; 424/401
(58) Field of Classification Search ........................ None
See application file for complete search history.

(56) References Cited

U.S. PATENT DOCUMENTS

| | | | |
|---|---|---|---|
| 6,200,680 B1 * | 3/2001 | Takeda et al. | 428/402 |
| 6,822,036 B1 * | 11/2004 | Gorl et al. | 524/492 |
| 2004/0202626 A1 * | 10/2004 | Wang et al. | 424/63 |
| 2007/0083001 A1 | 4/2007 | Amrhein et al. | |

FOREIGN PATENT DOCUMENTS

| | | |
|---|---|---|
| EP | 1 142 934 A2 | 10/2001 |
| EP | 1 288 248 A2 | 3/2003 |
| EP | 1 388 557 A2 | 2/2004 |
| WO | WO 97/36953 A1 | 10/1997 |
| WO | WO 00/58384 A1 | 10/2000 |
| WO | WO 2005/047344 A1 | 5/2005 |

OTHER PUBLICATIONS

Weber et al (WO9950339 A1), machine English translation.*

* cited by examiner

*Primary Examiner* — Brandon Fetterolf
*Assistant Examiner* — Jean Cornet
(74) *Attorney, Agent, or Firm* — Birch, Stewart, Kolasch & Birch, LLP

(57) ABSTRACT

Resin particles are produced by adding a liquid material having a boiling point of 100° C. or higher to an aqueous dispersion of resin particles to yield a mixture, recovering a wet cake from the mixture by filtration, and drying the wet cake. A water-soluble material is preferably used as the liquid material. The liquid material may also be at least one compound selected from compounds listed in The Japanese Standards of Cosmetic Ingredients, The Japanese Cosmetic Ingredients Codex, The Pharmacopoeia of Japan, and The Japan's Specifications and Standards for Food Additives. According to this method, there are provided resin particles which are resistant to coagulation upon drying and are satisfactorily dispersible in other materials.

11 Claims, No Drawings

METHOD FOR THE PRODUCTION OF RESIN PARTICLES

TECHNICAL FIELD

The present invention relates to methods for the production of resin particles for use as components typically in coating materials, cosmetics, and toners.

BACKGROUND ART

Resin particles are granular particles and are widely used as additives for use in other materials. They can be produced, for example, separating resin particles as a wet cake from an aqueous dispersion (latex) of resin granules dispersed in water, and drying the separated resin particles. However, such particles are susceptible to coagulation with each other upon drying or are poorly dispersed when the dried resin particles are added to other materials.

As a possible solution to prevent the coagulation of particles upon drying, Japanese Unexamined Patent Application Publication (JP-A) No. 59-155402, for example, discloses a technique for the production of a thermoplastic resin, including the steps of coagulating latex particles, removing free water, separating latex particles as a wet cake, adding a flowability-imparting agent to the wet cake, and spray drying the resulting mixture. Japanese Unexamined Patent Application Publication (JP-A) No. 59-22905 discloses a technique of granulating particles having a high bulk density and capable of absorbing a plasticizer satisfactorily, by adding a hydrophobic substance to the wet cake.

All these techniques, however, fail to sufficiently prevent the coagulation upon drying, because a flowability-imparting agent or a hydrophobic substance is added to a wet cake containing tightly adhered resin particles, does not cover entire surfaces of particles uniformly, and exposed surfaces of particles come in intimate contact with each other. In addition, the resulting resin particles have poor dispersibility, are thereby difficult to mix with other materials uniformly, and are limited, in use.

Patent Document 1: Japanese Unexamined Patent Application Publication (JP-A) No. 59-155402
Patent Document 2: Japanese Unexamined Patent Application Publication (JP-A) No. 59-22905

DISCLOSURE OF INVENTION

Problems to be Solved by the Invention

Accordingly, an object of the present invention is to provide a method for the production of resin particles that are resistant to coagulation upon drying and exhibit excellent dispersibility when added to other materials.

Another object of the present invention is to provide a method for the production of resin particles that have excellent safety in addition to the above-mentioned properties and are usable as additives for cosmetics.

Means for Solving the Problems

After intensive investigations to achieve the objects, the present inventors have found that resin particles being resistant to coagulation upon drying and having improved compounding properties with other materials can be obtained by adding a specific liquid material to an aqueous dispersion of resin particles and filtering the resulting dispersion. The present invention has been made based on these findings.

Specifically, according to the present invention, there is provided a method for the production of resin particles, including the steps of adding a liquid material having a boiling point of 100° C. or higher to an aqueous dispersion of resin particles to yield a mixture, recovering a wet cake from the mixture by filtration, and drying the wet cake to thereby yield resin particles. The liquid material may include a water-soluble material and preferably includes a dihydric or trihydric alcohol. The liquid material also preferably include at least one compound selected from compounds listed in The Japanese Standards of Cosmetic Ingredients, The Japanese Cosmetic Ingredients Codex, The Pharmacopoeia of Japan, and The Japan's Specifications and Standards for Food Additives.

Resin particles for use in the present invention may include a thermoplastic resin, and the thermoplastic resin may be a polyamide resin. According to the method for the production of resin particles according to the present invention, there is provided resin particles which may be used as components in cosmetics.

In a method for the production of resin particles according to the present invention, when the aqueous dispersion contains 100 parts by weight of the resin particles, "A" parts by weight of water, and "B" parts by weight of the liquid material, and the wet cake obtained as a result of filtration of the aqueous dispersion contains "C" percent by weight of water, the parameters "A", "B", and "C" preferably satisfy the following condition:

$$(100 \times B \times C)/[(100-C) \times (A+B)] = 0.01 \text{ to } 20.$$

Advantages

By carrying out a method according to the present invention, a liquid material can uniformly cover resin particles to thereby prevent coagulation of resin particles after drying, because the liquid material is added to an aqueous dispersion of resin particles before filtration. The resulting resin particles have excellent affinity for other materials and can be satisfactorily dispersed therein. In particular, resin particles produced by using a specific liquid material are highly safe and thereby useful as additives for cosmetics.

BEST MODE FOR CARRYING OUT THE INVENTION

An aqueous dispersion of resin particles for use in the present invention has only to contain resin particles and water as components.

A resin to constitute resin particles is not specifically limited, as long as it is a water-insoluble resin, and examples thereof include thermoplastic resins and thermosetting resins, of which thermoplastic resins are preferred. Such thermoplastic resins include, but are not limited to, polycondensation resins including polyamide resins such as polyamide 46, polyamide 6, polyamide 66, polyamide 612, polyamide 610, polyamide 910, polyamide 912, polyamide 1212, polyamide 1012, polyamide 1010, polyamide 11, polyamide 12, polyamide 6T, and polyamide 9, as well as polyester resins, polyurethane resins, poly (thio) ether resins, polycarbonate resins, polysulfone resins, and polyimide resins; vinyl-polymerization resins including polyolefin resins such as polyethylenes, polypropylenes, ethylene-propylene copolymers, and ethylene-acrylic acid copolymers, (meth)acrylic resins such as poly(methyl methacrylate)s, styrenic resins such as polystyrenes and styrene-acrylic acid polymers, and vinyl resins; and resins derived from naturally occurring substances such as cellulose derivatives. Each of these water-insoluble thermoplastic resins can be used alone or in combination.

Of the thermoplastic resins, polyamide resins, (meth)acrylic resins, styrenic resins, and polyurethane resins are preferred, and polyamide resins are typically preferred. In this connection, particles including a hydrophilic thermoplastic resin are seriously susceptible to coagulation due to evaporation of water upon drying. By a method according to the present invention, however, coagulation of such resin particles upon drying can be effectively prevented. The term "hydrophilic thermoplastic resin" means a resin having a hydrophilic group such as amido group, ester group, carboxyl group, or hydroxyl group, and examples of such hydrophilic thermoplastic resins include polyamide resins.

Resin particles have any shape as long as they are granular, and they can be, for example, spheroid such as spherical or oval, or spherical or rectangular columnar. The size of particles can be appropriately selected according to the use within ranges not adversely affecting the dispersibility. The size in terms of diameter or major axis is, for example, about 0.01 to about 300 μm and preferably about 0.1 to about 100 μm.

Resin particles may further include other components in addition to the above-exemplified resins. Examples of such other components include polymerizable monomers (residual monomers); crosslinking agents; surfactants; emulsifiers; fillers; plasticizers; flexibilizers; lubricants; stabilizers such as thermal stabilizers, antioxidants, and ultraviolet absorbers; thickening agents; colorants such as titanium oxide, carbon black, and pigments; metal powders; dispersing agents; flame retardants; and antistatic agents.

Resin particles can be prepared according to a known procedure using a resin as exemplified above and, where necessary, other materials. They can be prepared, for example, as spheroid resin particles by subjecting a polymerizable monomer typically to emulsion polymerization or suspension polymerization in a mixture of water and an organic solvent. Spheroid resin particles such as spherical resin particles can also be prepared by preparing a resin composition containing fine resin particles dispersed in a water-soluble material as a matrix, and washing the composition with water to dissolve and remove the water-soluble material.

The content of resin particles in the entire aqueous dispersion is, for example, about 5 to about 70 percent by weight, and preferably about 10 to about 65 percent by weight. If the concentration (content) is less than 5 percent by weight, the productivity may deteriorate, and if it exceeds 70 percent by weight, the resin particles may become difficult to be dispersed uniformly.

An aqueous dispersion of resin particles can be prepared by uniformly dispersing the resin particles in water typically with stirring. In addition to the resin particles and water, the aqueous dispersion may further contain other components, such as a dispersing agent, within ranges not adversely affecting advantages of the present invention as described later.

It is important according to the present invention to add a liquid material having a boiling point of 100° C. or higher under atmospheric pressure (at an absolute pressure of 0.10 MPa or less under normal pressure) to an aqueous dispersion to yield a mixture and to carry out the filtration of the mixture. Entire surfaces of dispersed individual resin particles can be coated with a liquid material by adding the liquid material to the aqueous dispersion. This highly effectively prevents adhesion/coagulation of resin particles with each other, and independent individual resin particles are thus obtained. If the boiling point is lower than 100° C., the liquid material volatilizes together with evaporation of water as a result of heating for drying of resin particles. Thus, part or all of the resin particles are exposed without being coated with the liquid material, and the resin particles become in intimate contact with each other and thereby coagulate. Liquid materials having a boiling point of 120° C. or higher under atmospheric pressure are preferred, of which those having a boiling point of 150° C. or higher under atmospheric pressure are more preferred. This is because such liquid materials are more resistant to volatilization accompanied with evaporation of water and further prevent the coagulation of resin particles upon drying more effectively.

Examples of liquid materials having a boiling point of 100° C. or higher under atmospheric pressure include water-soluble materials and water-insoluble materials and can be appropriately selected according typically to the type of resin constituting resin particles. Examples of water-soluble materials include monohydric alcohols having four or more carbon atoms, such as butanol, pentanol, and hexanol; and polyhydric alcohols including dihydric alcohols such as ethylene glycol, propanediols (1,2-propanediol and 1,3-propanediol), butanediols (e.g., 1,2-butanediol and 1,3-butanediol), pentanediols, and nonanediols, and trihydric alcohols such as glycerol. Examples of water-soluble materials further include polyalkylene glycols such as diethylene glycol, triethylene glycol, polyethylene glycol, dipropylene glycol, and polypropylene glycol; glycol ethers such as ethylene glycol monomethyl ether, ethylene glycol dimethyl ether, propylene glycol monomethyl ether, ethylene glycol monoethyl ether, ethylene glycol diethyl ether, and propylene glycol monomethyl ether; and glycol ether acetates such as ethylene glycol monomethyl ether acetate, propylene glycol monomethyl ether acetate, ethylene glycol monoethyl ether acetate, and propylene glycol monoethyl ether acetate. The water-soluble materials further include surfactants such as nonionic, anionic, and cationic surfactants. The water-insoluble materials are believed to prevent the coagulation of resin particles by precipitating and coating the resin particles upon filtration of the aqueous dispersion. Examples of the water-insoluble materials include hydrocarbons including aliphatic hydrocarbons having eight or more carbon atoms, such as octane, nonane, decane, and liquid paraffin; and alicyclic hydrocarbons having seven or more carbon atoms, such as cycloheptane, cyclooctane, and cyclononane.

Of these materials, water-soluble materials are preferred, because they are easily dispersed in an aqueous dispersion and can uniformly cover resin particles to thereby effectively prevent the adhesion/coagulation of resin particles with each other. Among them, dihydric alcohols and trihydric alcohols are more preferably used. Such water-soluble materials are also advantageous in having excellent affinity for hydrophilic resin particles. In contrast, water-insoluble materials are advantageously used in the production of hydrophobic resin particles, of which liquid paraffin is more preferably used.

Liquid materials for use in the present invention also include, for example, compounds listed in The Japanese Standards of Cosmetic Ingredients, The Japanese Cosmetic Ingredients Codex, The Pharmacopoeia of Japan, and The Japan's Specifications and Standards for Food Additives. When these compounds are used as a liquid material, the liquid material is safe even when resides in dried resin particles, and the dried resin particles can be added to other materials without further treatment. A material to be used in cosmetics to which dried resin particles are added is more preferably used as the liquid material.

The amount of the liquid material is not specifically limited, as long as the liquid material can uniformly cover surfaces of dried resin particles. The amount can be selected as appropriate according typically to the amount of resin particles, the solid content of the aqueous dispersion, and the water content of the wet cake after filtration. The amount of such a liquid material is, for example, about 0.2 to about 30 parts by weight, preferably about 0.5 to about 15 parts by weight, and more preferably about 1 to about 10 parts by weight, to 100 parts by weight of the resin. If the amount is less than 0.2 parts by weight, the liquid material may not sufficiently cover surfaces of resin particles, and this may often cause coagulation of resin particles. In contrast, the amount exceeding 30 parts by weight is not economical.

Other components may be added to the aqueous dispersion, in addition to the liquid material.

A mixture mainly containing water, a liquid material, and resin particles is subjected to filtration to remove free water from the mixture to thereby recover a wet cake including the resin particles. The filtration can be carried out according to a conventional procedure typically using a filter, and can be carried out under normal pressure, under a pressure (under a load), or under reduced pressure. The water content of the wet cake is, for example, 50 percent by weight or less (e.g., 10 to 50 percent by weight), preferably 40 percent by weight or less (e.g., 15 to 40 percent by weight), and typically preferably 35 percent by weight or less (e.g., 15 to 35 percent by weight). If the water content is excessively high, the production efficiency of resin particles may often deteriorate, because it takes a much time to dry the wet cake. In contrast, if it is excessively low, the liquid material may be discharged (removed) together with filtrated water from the mixture as a result of filtration to yield a wet cake. Thus, the liquid material may not sufficiency uniformly cover surfaces of resin particles, and this may cause coagulation of resin particles. According to the present invention, adhesion of resin particles with each other can be prevented, even when resin particles are recovered as a wet cake. This is because filtration is carried out after adding a liquid material to the aqueous dispersion to thereby allow the liquid material to cover entire surfaces of the resin particles.

The wet cake recovered by the filtration is dried to thereby yield resin particles. The drying can be carried out typically using a heating device such as a heater or hot air, and can be conducted either under normal pressure or under reduced pressure. The drying temperature can be any temperature, as long as water can evaporate, or higher. The temperature is preferably equal to or higher than the boiling point of water at the pressure during drying and equal to or lower than the boiling point of the liquid material. When drying is carried out under normal pressure, the temperature is generally about 60° C. or higher, for example, about 60° C. to about 200° C., and preferably about 80° C. to about 150° C. When the drying is carried out under reduced pressure, the drying temperature is, for example, about 40° C. to about 120° C. Resin particles constituting a wet cake are in intimate contact with each other and thereby often undergo coagulation upon evaporation of water as a result of heating. According to the present invention, however, the coagulation of resin particles upon drying can be significantly prevented, because a liquid material having a boiling point of 100° C. or higher is used, and the liquid material does not evaporate and keeps to cover the resin particles even when a wet cake is heated to evaporate water.

According to a preferred embodiment of present invention, resin particles are produced, for example, by adding a water-soluble material as a liquid material to an aqueous dispersion containing resin particles dispersed in water, stirring the mixture to yield a homogenous dispersed mixture, subjecting the dispersed mixture to filtration under reduced pressure to thereby recover a wet cake including resin particles, and heating and drying the wet cake at a temperature of about 100° C.

The dried resin particles preferably still contain a residual liquid material to some extent in the method according to the present invention. The content [percent by weight] of the liquid material in the dried resin particles can be expressed as the value calculated according to the expression:

$$[(100 \times B \times C)/\{(100-C) \times (A+B)\}] \times 100$$

$$[(100 \times B \times C)/\{(100-C) \times (A+B)\}] \div 100$$

wherein the aqueous dispersion contains 100 parts by weight of the resin particles, "A" parts by weight of water, and "B" parts by weight of the liquid material, and wherein the wet cake obtained as a result of filtration of the aqueous dispersion contains "C" percent by weight of water. The value, thus calculated, is preferably 0.01 to 20 in the present invention. Namely, the content of the liquid material in the dried resin particles is preferably within a range of 0.01 to 20 parts by weight, to 100 parts by weight of the resin particles. If the content is less than 0.01 parts by weight, coagulation of particles upon drying may not be sufficiently effectively prevented, and the particles may not have so effectively improved dispersibility. If it exceeds 20 parts by weight, particles may form a slurry and the dried particles may often become difficult to handle.

The expression can be introduced in the following manner. Specifically, the amount of the entire wet cake is $100/\{(100-C)/100\}$ parts by weight, because the water content of the wet cake as a result of filtration is "C" percent by weight, and the solid content of the wet cake (content of resin particles) is 100 parts by weight. The amount of aqueous components (water and the liquid material) is therefore expressed by: $100/\{(100-C)/100\}-100=100 \times C/(100-C)$ parts by weight. The liquid material is uniformly dispersed in water, and the ratio of the liquid material in the aqueous components is expressed by $B/(A+B)$. Accordingly, the content of the liquid material in the wet cake is expressed by: $100 \times C/(100-C) \times B/(A+B) = (100 \times B \times C)/\{(100-C) \times (A+B)\}$ parts by weight.

By a method according to the present invention, resin particles can be efficiently produced as independent individual resinous polymer particles without coagulation upon drying. In particular, when hydrophilic resin particles are produced according to the method, coagulation can be more effectively prevented by using, as a liquid material, a water-soluble material having high affinity for the resin to thereby cover surfaces of resin particles uniformly. When resin particles are produced by using, as a liquid material, a material constituting cosmetics to which the resin particles are to be compounded, the resulting resin particles can be safely used as additives for the cosmetics, even when the liquid material resides in the resin particles after drying.

Resin particles produced by a method according to the present invention are highly dispersible and can be uniformly mixed with other materials. Such resin particles can be used, for example, in various materials such as coating materials, cosmetics, and toners and are typically useful as resin particles for use in cosmetics.

EXAMPLES

The present invention will be illustrated in further detail with reference to several examples below, which, however, by no means limit the scope of the present invention. The term "water content" indicates the percentage of weight loss after drying a wet cake (5 g) in an air dryer at 130° C. to a constant weight. These results are shown in Table 1. In Table 1, the numeral in "Coagulation property" indicates the ratio [percent by weight] of resin particles passed through a sieve (300-mesh) to the dried cake.

Example 1

An aqueous dispersion was prepared by uniformly dispersing 100 parts by weight of spherical particles of polyamide 12 having a median diameter of 5 μm in 200 parts by weight of water. The aqueous dispersion was mixed with 3 parts by weight of 1,3-butanediol having a boiling point of 208° C. as a liquid material, followed by stirring to yield a slurry. The slurry was filtrated though a 5A filter paper under reduced pressure to thereby recover a wet cake. The wet cake had a water content of 30 percent by weight. The recovered wet cake was dried in a dryer at 100° C. for four hours. The dried cake was placed together with silicone balls on a 300-mesh sieve, the sieve was lidded and shaken by hand for three minutes to thereby remove coagulated resin particles. Thus, resin particles were obtained, in which 82 percent by weight of the dried cake passed through the sieve as resin particles.

Example 2

Resin particles were produced by the procedure of Example 1, except for adding 10 parts by weight of 1,3-butanediol. The wet cake had a water content of 31 percent by weight, and 90 percent by weight of the dried cake passed through the sieve as resin particles.

Example 3

Resin particles were produced by the procedure of Example 1, except for adding 3 parts by weight of glycerol having a boiling point of 290° C. as a liquid material instead of 1,3-butanediol. The wet cake had a water content of 29 percent by weight, and 80 percent by weight of the dried cake passed through the sieve as resin particles.

Example 4

Resin particles were produced by the procedure of Example 1, except for adding 3 parts by weight of liquid paraffin having a boiling point of 300° C. or higher as a liquid material instead of 1,3-butanediol. The wet cake had a water content of 30 percent by weight, and 67 percent by weight of the dried cake passed through the sieve as resin particles.

Example 5

Resin particles were produced by the procedure of Example 1, except for using 100 parts by weight of water and adding 3 parts by weight of 1,3-butanediol as a liquid material. The wet cake had a water content of 32 percent by weight, and 86 percent by weight of the dried cake passed through the sieve as resin particles.

Example 6

Resin particles were produced by the procedure of Example 1, except for adding 3 parts by weight of particles of polyamide 6 as resin particles instead of the particles of polyamide 12. The wet cake had a water content of 30 percent by weight, and 80 percent by weight of the dried cake passed through the sieve as resin particles.

Comparative Example 1

Resin particles were produced by the procedure of Example 1, except for not adding 1,3-butanediol. The wet cake had a water content of 31 percent by weight, and 40 percent by weight of the dried cake passed through the sieve as resin particles.

Comparative Example 2

Resin particles were produced by the procedure of Example 1, except for adding 3 parts by weight of ethanol having a boiling point of 78° C. as a liquid material instead of 1,3-butanediol. The wet cake had a water content of 30 percent by weight, and 45 percent by weight of the dried cake passed through the sieve as resin particles.

Evaluation

Dispersibility in Water

Resin particles (20 g) passed through the sieve as obtained in Examples and Comparative Examples were mixed with 80 g of distilled water and dispersed therein by application of ultrasound for three minutes. The dispersion of the particles was observed under a microscope at a magnification of 800 times. A sample showing independent individual particles within a visual field (circle having a diameter of 200 μm) was evaluated as "Good", a sample showing one to three coagulant including several particles was evaluated as "Fair", and a sample showing four or more coagulants was evaluated as "Failure" in dispersibility in water. These results are shown in Table 1.

Amount of Residual Liquid Material in Resin Particles

The amounts of residual liquid materials in resin particles prepared according to Examples and Comparative Examples were determined by calculation according to the expression: $(100 \times B \times C)/\{(100-C) \times (A+B)\}$, wherein the aqueous dispersion contains 100 parts by weight of the resin particles, "A" parts by weight of water, and "B" parts by weight of the liquid material, and wherein the wet cake contains "C" percent by weight of water. These results are shown in "Amount of residual liquid material" in Table 1.

[Table 1]

TABLE 1

| | Liquid material Type [parts by weight] | Wet cake Water content [weight %] | Coagulation property [weight %] | Dispersibility in water | Amount of residual liquid material [parts by weight] |
|---|---|---|---|---|---|
| Example 1 | 1,3-Butanediol [3] | 30 | 82 | Good | 0.63 |
| Example 2 | 1,3-Butanediol [10] | 31 | 90 | Good | 2.14 |
| Example 3 | Glycerol [3] | 29 | 80 | Good | 0.60 |
| Example 4 | Liquid paraffin [3] | 30 | 67 | Fair | 0.63 |

TABLE 1-continued

|  | Liquid material Type [parts by weight] | Wet cake Water content [weight %] | Coagulation property [weight %] | Dispersibility in water | Amount of residual liquid material [parts by weight] |
|---|---|---|---|---|---|
| Example 5 | 1,3-Butanediol [3] | 32 | 86 | Good | 1.37 |
| Example 6 | 1,3-Butanediol [3] | 30 | 80 | Good | 0.63 |
| Com. Ex. 1 | — | 31 | 40 | Failure | 0 |
| Com. Ex. 2 | Ethanol [3] | 30 | 45 | Failure | 0.63 |

The invention claimed is:

1. A method for the production of resin particles, comprising the steps of:
adding a liquid material having a boiling point of 100° C. or higher to an aqueous dispersion consisting of water-insoluble thermoplastic resin particles and water to yield a mixture, recovering a wet cake from the mixture by filtration, and
drying the wet cake to thereby yield resin particles;
wherein the aqueous dispersion contains 100 parts by weight of the resin particles, "A" parts by weight of water, and "B" parts by weight of the liquid material, wherein the wet cake obtained as a result of filtration of the aqueous dispersion contains "C" percent by weight of water, and wherein the parameters "A", "B", and "C" satisfy the following condition:

$$(100 \times B \times C)/[(100-C) \times (A+B)] = 0.60 \text{ to } 20;$$

wherein each individual resin particle is coated with the liquid material to form an independent coated resin particle;
wherein the amount of the liquid material in the dispersion is from 0.2 to 30 parts by weight to 100 parts by weight of the resin; and
wherein the liquid material is at least one selected from the group consisting of a monohydric alcohol, dihydric alcohol, trihydric alcohol, polyhydric alcohol, polyalkylene glycol, glycol ether and glycol ether acetate.

2. The method for the production of resin particles according to claim 1, wherein the liquid material comprises a water-soluble material.

3. The method for the production of resin particles according to claim 1, wherein the thermoplastic resin is a polyamide resin.

4. The method for the production of resin particles according to claim 1, wherein the resin particles are used in cosmetics.

5. The method for the production of resin particles according to claim 1, wherein the liquid material is at least one selected from the group consisting of butanol, pentanol, hexanol, ethylene glycol, propanediol, butanediol, pentanediol, nonanediol, glycerol, diethylene glycol, triethylene glycol, polyethylene glycol, dipropylene glycol, polypropylene glycol, ethylene glycol monomethyl ether, ethylene glycol dimethyl ether, propylene glycol monomethyl ether, ethylene glycol monoethyl ether, ethylene glycol diethyl ether, propylene glycol monomethyl ether, ethylene glycol monomethyl ether acetate, propylene glycol monomethyl ether acetate, ethylene glycol monoethyl ether acetate, and propylene glycol monoethyl ether acetate.

6. The method for the production of resin particles according to claim 1, wherein the liquid material has a boiling point of 120° C. or higher.

7. The method for the production of resin particles according to claim 1, wherein a coagulation property of resin particles is 80 percent by weight or more, and the numeral in the coagulation property indicates the ratio [percent by weight] of resin particles which have passed through a sieve (300-mesh) to the dried cake.

8. Resin particles produced by the method according to claim 1.

9. An additive for cosmetics comprising the resin particles according to claim 8.

10. A method for producing a cosmetic comprising adding the resin particles according to claim 8.

11. A method for producing a cosmetic comprising adding the additive for cosmetics according to claim 9.

* * * * *